United States Patent
Li et al.

(10) Patent No.: US 6,905,708 B2
(45) Date of Patent: Jun. 14, 2005

(54) CONTROLLED RELEASE ORAL DOSAGE FORM

(75) Inventors: Boyong Li, Davie, FL (US); Avinash Nangia, Weston, FL (US); Chih Ming Chen, Davie, FL (US); Xiu Xiu Cheng, Davie, FL (US)

(73) Assignee: ANDRX Pharmaceuticals, Inc., Davie, FL (US)

( * ) Notice: Subject to any disclaimer, the term of this patent is extended or adjusted under 35 U.S.C. 154(b) by 77 days.

(21) Appl. No.: 10/435,012

(22) Filed: May 9, 2003

(65) Prior Publication Data

US 2003/0198683 A1 Oct. 23, 2003

Related U.S. Application Data

(60) Division of application No. 10/071,257, filed on Feb. 8, 2002, and a continuation-in-part of application No. 09/905,712, filed on Feb. 8, 2001, and a continuation-in-part of application No. 09/905,690, filed on Feb. 8, 2001, each is a continuation-in-part of application No. 09/259,133, filed on Feb. 26, 1999, now Pat. No. 6,210,716.

(51) Int. Cl.[7] .............................. A61K 9/14; A61K 9/48; A61K 9/54

(52) U.S. Cl. ....................... 424/489; 424/490; 424/457; 424/458

(58) Field of Search ................................ 424/497, 489, 424/490, 457, 458

(56) References Cited

U.S. PATENT DOCUMENTS

| | | |
|---|---|---|
| 2,987,445 A | 6/1961 | Levesque |
| 3,146,169 A | 8/1964 | Stephenson et al. |
| 3,538,214 A | 11/1970 | Polli et al. |
| 3,773,920 A | 11/1973 | Nakamoto et al. |
| 3,819,706 A | 6/1974 | Mehta |
| 3,885,046 A | 5/1975 | Mehta |
| 4,016,880 A | 4/1977 | Theeuwes et al. |
| 4,135,514 A | 1/1979 | Zaffaroni et al. |
| 4,173,626 A | 11/1979 | Dempski et al. |
| 4,309,405 A | 1/1982 | Guley et al. |
| 4,327,725 A | 5/1982 | Cortese et al. |
| 4,393,078 A | 7/1983 | Peck |
| 4,435,449 A | 3/1984 | Stern |
| 4,438,138 A | 3/1984 | Stern |
| 4,507,323 A | 3/1985 | Stern |
| 4,519,801 A | 5/1985 | Edgren |
| 4,539,198 A | 9/1985 | Powell et al. |
| 4,557,925 A | 12/1985 | Lindahl et al. |
| 4,571,395 A | 2/1986 | Peck |
| 4,687,660 A | 8/1987 | Baker et al. |
| 5,098,715 A | 3/1992 | McCabe et al. |
| RE33,994 E | 7/1992 | Baker et al. |
| 5,358,970 A | 10/1994 | Ruff et al. |
| 5,427,798 A | 6/1995 | Ludwig et al. |
| 5,472,708 A | 12/1995 | Chen |
| 5,478,577 A | 12/1995 | Sackler et al. |

(Continued)

FOREIGN PATENT DOCUMENTS

WO    WO 00/30685    6/2000

OTHER PUBLICATIONS

Physicians' Desk Reference 46th Edition 1992 p. 821 "Wellbutrin".

Cooper et al., Journal of Pharmaceutical Sciences, vol. 73, No. 8 Aug. 1984; "Determination of Bupropion and Its Major Basic Metabolites in Plasma by Liquid Chromatography with Dual–Wave Ultraviolet Detection" pp. 1104–1107.

*Primary Examiner*—James M. Spear
(74) *Attorney, Agent, or Firm*—Hedman & Costigan, P.C.

(57) ABSTRACT

A once a day bupropion hydrochloride formulation is disclosed

6 Claims, 4 Drawing Sheets

U.S. PATENT DOCUMENTS

| | | |
|---|---|---|
| 5,508,040 A | 4/1996 | Chen |
| 5,508,042 A | 4/1996 | Oshlack et al. |
| 5,512,593 A | 4/1996 | Dante |
| 5,541,231 A | 7/1996 | Ruff et al. |
| 5,672,360 A | 9/1997 | Sackler et al. |
| 5,731,000 A | 3/1998 | Ruff et al. |
| 5,763,493 A | 6/1998 | Ruff et al. |
| 5,837,379 A | 11/1998 | Chen et al. |
| 5,968,553 A | 10/1999 | Maitra et al. |
| 5,990,175 A | 11/1999 | Pinsker |
| 6,033,686 A | 3/2000 | Seth |
| 6,096,341 A | 8/2000 | Seth |
| 6,110,973 A | 8/2000 | Young |
| 6,143,327 A | 11/2000 | Seth |
| 6,150,420 A | 11/2000 | Houdi et al. |
| 6,194,002 B1 | 2/2001 | Sherman |
| 6,197,827 B1 | 3/2001 | Cary |
| 6,210,716 B1 | 4/2001 | Chen et al. |
| 6,221,917 B1 | 4/2001 | Maitra et al. |
| 6,238,697 B1 | 5/2001 | Kumar et al. |
| 6,242,496 B1 | 6/2001 | Kulkarni et al. |
| 6,277,887 B1 | 8/2001 | Young |
| 6,280,763 B1 | 8/2001 | Midha et al. |
| 6,306,436 B1 | 10/2001 | Chungi et al. |
| 6,312,716 B1 | 11/2001 | Midha et al. |
| 6,333,332 B1 | 12/2001 | Han et al. |
| 6,337,328 B1 | 1/2002 | Fang et al. |
| 6,342,496 B1 | 1/2002 | Jerussi et al. |
| 6,369,113 B2 | 4/2002 | Young |
| 6,589,553 B2 | 7/2003 | Li et al. |

CONTROLLED RELEASE ORAL DOSAGE FORM

CROSS REFERENCE TO RELATED APPLICATIONS

The present invention is a divisional of application Ser. No. 10/071,257, filed Feb. 8, 2002, and claims is a continuation-in-part of the converted nonprovisional application Ser. No. 09/905,712 of U.S. Provisional Application Ser. No. 60/267,457, filed Feb. 8, 2001 and the converted nonprovisional application Ser. No. 09/905,690 of U.S. Provisional Application Ser. No. 60/267,456, filed Feb. 8, 2001, which converted nonprovisional applications are in turn a continuation-in-part of application Ser. No. 09/259,133, filed Feb. 26, 1999, now U.S. Pat. No. 6,210,716.

FIELD OF THE INVENTION

The present invention relates to oral controlled release dosage formulations containing bupropion hydrochloride.

BACKGROUND OF THE INVENTION

The compound designated bupropion hydrochloride is described in U.S. Pat. Nos. 3,819,706 and 3,885,046. It is marketed as an anti-depressant and an aid to smoking cessation. Bupropion is an aminoketone-derivative chemically unrelated to other currently available antidepressants (e.g., selective serotonin-reuptake inhibitors, tricyclics, tetracyclics).

While the neurochemical mechanisms of the antidepressant and smoking cessation effects are unknown, noradrenergic pathways and/or dopaminergic effects appear to be primarily involved. Bupropion does not inhibit monoamine oxidase and is a weak blocker of serotonin and norepinephrine uptake.

The drug is useful in the treatment of depressive affective disorders (e.g., major depression) at dosages of 75 to 600 mg daily. Bupropion may be preferable to other agents because of its minimal anticholinergic, cardiovascular, and antihistaminic effects or in those patients who have experienced weight gain or sexual dysfunction with another antidepressant. Bupropion, as extended-release tablets, is used in the cessation of smoking at dosages of 100–300 mg daily. Withdrawal symptoms and cigarette craving are reduced with bupropion. Other uses include patients with bipolar depression, attention-deficit hyperactivity in both adult and pediatric patients, and panic symptoms superimposed on depression.

Immediate release bupropion tablets provide more than 75% of bupropion release into the dissolution media in 45 minutes. In studies to date, the risk of seizures appears to be strongly associated, in part, with the use of instant release tablets.

Numerous techniques exist in the prior art for preparing sustained or controlled release pharmaceutical formulations. One common technique involves surrounding an osmotically active drug core with a semipermeable membrane. The drug is released from the core over time by allowing a fluid such as gastric or intestinal fluid to permeate the coating membrane and dissolve the drug so the dissolved drug can permeate through the membrane. In some cases a hydrogel is employed to push the active ingredient through the passageway of the membrane.

Another common technique for preparing controlled-release pharmaceutical formulations is to encapsulate a plurality of beads, pellets or tablets that are coated with varying levels of diffusion barriers. The barriers can be of the same or different chemical composition. Release of the pharmaceutical may occur by leaching, erosion, rupture, diffusion or similar actions depending on the nature and thickness of the coating material. These products require multi-layered coating, sometimes as much as 30 to 90 coats.

Film coating techniques are characterized by the deposition of a uniform film onto the surface of a substrate. Because of the capability of depositing a variety of coating materials onto solid cores, this process has been used to make controlled release dosage forms starting from different formulations, such as tablets, granules, pellets and capsules. Cores are usually prepared using one of the following processes: compaction, surface layering, or agglomeration.

One limitation associated with these dosage forms consists in their failure to delay drug delivery. Many of the multi-walled preparations described above do not provide prolonged delayed release of the drug prior to initiation of sustained release, which is important when biphasic release profiles are desired. Other systems are essentially "delayed" releases mechanisms. There is delay of drug release in the stomach, but once the coated drug reaches the intestines, the release of medication is rapid. There is no sustained release in the intestines.

Bupropion hydrochloride is highly soluble in water with a high permeability characterized by rapid and almost complete absorption. Peak plasma concentrations occur within 2 hours for bupropion and 3 hours for bupropion sustained-release. Its biphasic pharmacokinetics is characterized by a two-compartment model; the distributive phase has a mean half-life of 3 to 4 hours with a biphasic decline and a terminal T ½ of about 14 hours following single doses. A major drawback is extensive first-pass metabolism. It appears that only a small portion of any oral dosage reaches the systemic circulation intact. Immediate-release tablets are dosed three times a day, preferably with 6 or more hours separating the doses. For those patients requiring doses greater than 300 mg daily, each divided dose should not exceed 150 mg each. This necessitates administration of the tablets 4 times daily with at least 4 hours between successive doses. Commercially available sustained-release products are available in film-coated tablets marketed by Glaxo Wellcome under the tradenames Wellbutrin® SR and Zyban®. These are dosed twice daily. For those patients requiring above 300 mg daily, the regimen remains twice daily dosing. No currently available product provides a sustained release profile suitable for once daily dosing.

Patient compliance is especially problematic in depressed patients. There is a need for improved patient compliance. One of the means employed clinically to improve patient adherence to therapy is simplification of the dosing regimen. Thus, need exists for a once daily bupropion formulation.

Sustained release tablet forms of bupropion are described in U.S. Pat. No. 5,427,798, comprising a sustained release tablet which provides peak bupropion blood levels at approximately 2–3 hours, thereby requiring twice daily dosing. Controlled release is achieved by combining bupropion particles with microcrystalline cellulose and hydrogel-forming hydroxypropyl methylcellulose.

Another sustained release bupropion tablet or caplet formulation disclosed in U.S. Pat. No. 4,687,660, comprises a difficult manufacturing process and limited shelf life. U.S. Pat. No. 5,358,970 discloses a formulation of bupropion hydrochloride that contains an acid stabilizer.

U.S. Reissue Pat. No. 33,994 discloses a tablet formulation of a water insoluble, water-permeable film coating surrounding the drug core and a particulate, water-soluble, pore-forming material dispersed within the film coating, this osmotic gradient and channel forming system is applicable for tablet dosage forms. However, here also at least twice daily dosing is necessitated by the release profile of 25–70% of bupropion within 4 hours, and 40–90% within 6 hours. Wellbutrin® SR is a commercially available twice a day dosage form of bupropion which contains carnauba wax, cysteine hydrochloride, hydroxypropyl methylcellulose, magnesium stearate, microcrystalline cellulose, polyethylene glycol and titanium dioxide.

There is no capsule form of bupropion commercially available Capsules are advantageous in those patients who have difficulty swallowing where the contents of the capsule may be sprinkled on food.

Immediate release tablets must be stored at a temperature above 15–25° C. and protected from light and moisture. Extended-release tablets should be stored in tight, light-resistant containers at a temperature of 20–25° C.

The need exists for a delayed, sustained release pharmaceutical preparation that provides a longer delay of drug dissolution thereby allowing greater flexibility in designing sustained release profiles, provides improved plasma levels wherein the maximum plasma concentration ($C_{max}$) can be substantially reduced without a concomitant reduction in AUC, and is simply and economically produced. Such a delayed delivery dosage form has a practical application, and it represents a valuable contribution to the medical arts. The present invention provides such a composition, and offers an efficient and cost effective method of preparation.

Accordingly, it is an object of this invention to provide a sustained release formulation of bupropion suitable for once daily administration.

Another object of the present invention is to provide a capsule dosage form comprising means for delaying delivery of the drug in gastric fluids for 6 hours up to 12 hours, usually 4 hours to 8 hours.

It is also an object of this invention to provide a controlled and extended release bupropion capsule formulation that is easy to manufacture and can be used to prepare a range of dosing levels suitable for once daily administration.

It is a further object of the present invention to provide 24-hour control of symptoms of depression or tobacco dependence withdrawal.

Seizures result more commonly by single dosages of bupropion over 150 mg, hence the need for twice to four times daily dosing regimens. Another object of this invention is to provide simplified once daily dosing regimen with the potential to prevent or reduce the incidence of seizures caused by bupropion.

The present invention also relates to a new sustained release bupropion pharmaceutical composition producing novel blood plasma levels after ingestion over 24 hours that is not disclosed in, nor rendered obvious by, the prior art Other objects, features and advantages of the invention are not taught in the prior art but will be more apparent to those versed in the art from the following specification, taken in conjunction with the drawings.

SUMMARY OF THE PRESENT INVENTION

The present invention meets the unfulfilled needs of the pharmaceutical industry.

The current invention involves a new pelletization process, typified by the application of a bupropion/cellulose ether suspension to inert spheres and two unique formulations of sustained release coatings that are applied to separate active pellets. The formulation functions by membrane-controlled extended-release in a pH dependent manner. The bupropion release rate has been improved by the introduction of two types of film coated active pellets that release the drug at different pH resulting in novel dissolution profiles.

Inert spheres are initially coated with bupropion and hydroxypropyl methylcellulose. The active pellets containing bupropion comprise 70–75 weight % of the dosage form. An enteric coating, applied to about one third of the active drug pellets, is comprised of a film insoluble at low pH, such as hydroxypropyl methylcellulose phthalate. The second coating applied to the other two thirds of active drug pellets is comprised of a combination of a hydrophobic coating agent and methyl acrylic acid copolymer. The two pellet types are then combined in a capsule. Generally, the weight ratio of the first pellet to the second pellet will be from about 90:10 to about 10:90, although a weight ratio of from about 30:70 to about 70:30 is preferred. Especially preferred is a weight ratio of about 33.3:66.7.

This formulation can provide 24-hour efficacy with once daily dosing, with less than 50% of the drug released at 10 hours. Therapeutic plasma levels are maintained from 12 to 24 hours. The usual dosage range is 75–450 mg.

In another embodiment of the present, an uncoated bupropion component is also employed. In this embodiment, bupropion powder or granules, or the uncoated active pellets (bupropion and hydroxypropyl methylcellulose sprayed onto an inert sphere) may be used directly (first component). The bupropion release rate is further modified and improved by the introduction of uncoated bupropion and the two types of film coated active pellets that release the drug at different pH resulting in further novel dissolution profiles.

In this embodiment, the enteric coating (hydroxypropyl methylcellulose phthalate) is applied to from about 10 to about 90 weight percent of the active drug pellets (second component). The second coating (hydrophobic and methyl acrylic acid copolymer) is applied to from about 90 to about 10 weight percent of active drug pellets (third component). The three components are then combined in a capsule. Generally, the weight ratio of the first component to the second component may vary from about 1:50 to about 50:1, the weight ratio of the first component to the third component may vary from about 1:50 to about 50:1, and the weight ratio of the second component to the third component may vary from about 10:90 to about 90:10, although a weight ratio of from about 30:70 to about 70:30 is preferred. Especially preferred is a weight ratio of three components of about 10:30:60.

DETAILED DESCRIPTION OF THE PRESENT INVENTION

The present invention, in a first embodiment provides a two component controlled release bupropion formulation for oral administration, the formulation comprising:
(1) a first pellet comprising:
  (i) a core comprising:
    (a) bupropion and its salts, isomers, or a pharmaceutically acceptable aminoketone antidepressant agent;
    (b) an inert pellet as a starting material; and
    (c) a binder; and;
  (ii) a coating comprising:
    (a) a pH dependent coating agent;
    (b) a plasticizer; and
    (c) a lubricant, and
(2) a second pellet comprising:
  (i) a core comprising:
    (a) bupropion and its salts, isomers, or a pharmaceutically acceptable aminoketone antidepressant agent;
    (b) an inert pellet as a starting material; and
    (c) a binder; and
  (ii) a coating comprising:
    (a) a methyl acrylic acid copolymer;
    (b) a water insoluble polymer;
    (c) a plasticizer; and
    (d) an antisticking agent.

In other embodiments of the present invention, there may also be present another component, a form of immediate release bupropion.

The immediate release bupropion component may comprise any form of immediate release bupropion. This may take the form of uncoated bupropion granules or powders, may comprise bupropion active pellets (as described hereinbelow), may include bupropion granules or active pellets coated with a highly soluble immediate release coating, such as an Opadry® type coating, as are known to those skilled in the art (see generally, U.S. Pat. No. 5,098,715), or a combination of any of the foregoing.

The active pellets of bupropion hydrochloride useful in the practice of the present invention are preferably based on active pellets having a core forming inert component that may comprise any type of commonly known pellet starting material, which may be water insoluble, such as, but not limited to, cellulose spheres or silicon dioxide, or may be water soluble, such as, but not limited to, starch or sugar spheres having a diameter ranging from about 15 to about 50 mesh, preferably ranging from about 30 to about 35 mesh. The preferred pellet starting material is sugar spheres, NF, containing not less than about 62.5 percent and not more than about 91.5 percent of sucrose. The spheres should have consistent bulk density, low friability, and low dust generation properties.

The inert core is preferably coated with an aminoketone antidepressant agent or a pharmaceutically acceptable salt or stereoisomer thereof Most preferably, the core drug is bupropion hydrochloride.

The core forming inert component is coated with a formulation that comprises bupropion hydrochloride and a binding agent. The binding agent should be water soluble, and should possess high adhesivity and an appropriate viscosity, to guarantee good adhesion between the sugar cores and bupropion particles, resulting in a high concentration of drug in the pellets. The binding agents employed can be any type of binding agent commonly known in the art such as polyvinyl pyrrolidone, hydroxyethyl cellulose, hydroxypropyl cellulose, low molecular weight hydroxypropyl methylcellulose (HPMC), polymethacrylate or ethyl cellulose. In a preferred embodiment of the present invention, the binding agent is a water-soluble polymer such as hydroxypropyl methylcellulose having a viscosity in the range of 2–12 cps at 20° C., preferably 4–6 cps, such as the material sold as Methocel® E5. A preferred composition of the binder for bupropion is about 2–10% w/w, and most preferably 3–5%.

The active pellets of the present invention will preferably comprise the following ingredients:

| INGREDIENT | PREFERRED | MOST PREFERRED |
| --- | --- | --- |
| Bupropion HCl | 40–80% | 60–70% |
| HPMC | 2–10% | 2.5–5% |
| starting pellets | 10–35% | 15–30% |

All the percentages in the above-table are based on the total weight of the core.

The active pellets for use in the practice of the present invention that comprise the bupropion are typically prepared by forming a suspension of the binder and the drug and then layering the suspension onto the starting pellet using any of the layering techniques known in the industry, such as fluidized bed coating, rotor granulation or pan coating. The suspension medium may comprise any low viscosity solvent, such as isopropyl alcohol, ethanol, water, mixtures thereof and the like. A sufficient amount of coating is applied to provide the desired level of bupropion. These active pellets may be used directly as the first component of the three component formulations of the present invention.

The active pellets are also useful in preparing the other two components of the present invention (both the two component and three component formulations). The active pellets intended for such use are divided into two groups, each group receiving a film coating that releases the drug at a different pH. One group of pellets is coated to release drug at a pH corresponding to about 4.8 and lower, which is likely to occur in the upper gastrointestinal (GI) tract; the other group of pellets is film coated to release drug at a pH of 7 and above, which is likely to occur in the lower GI tract. Thus, the entire does is released from this product for an extended period of time during its transition through the GI tract.

In a preferred embodiment, one group of pellets (enteric component) is coated with a film comprising a pH dependent coating polymer, a plasticizer and a lubricant. This group of pellets preferably comprises from about 10 to about 90 weight percent of the total pellets, preferably from about 30 to about 70 weight percent, and most preferably from about 33 to about 60 weight percent.

The pH dependent coating polymer may be selected from those enteric coatings known to those skilled in the art Preferably, the pH dependent coating is selected from the group consisting of shellac, methacrylic acid copolymers (such as, but not limited to Eudragit® E100 (a cationic copolymer of dimethyl aminoethyl methacrylate and neutral methacrylic acid esters)), cellulose acetate phthalate, hydroxypropyl methylcellulose phthalate, hydroxypropyl methylcellulose acetate succinate, cellulose acetate trimellitate, polyvinyl acetate phthalate or mixtures thereof Hydroxypropyl methylcellulose phthalate (HPMCP) is preferred. The preferred concentration is 2–10% w/w of the total dosage form, and most preferably 3–5%.

The coating preferably also contains plasticizers. Plasticizers that may be used in the practice of the present invention include any of those known to those skilled in the art, including, but not limited to, acetyltributyl citrate, triacetin, acetylated monoglyceride, rape oil, olive oil, sesame oil, acetyltriethyl citrate, glycerin sorbitol, diethyloxalate, diethylmalate, diethylfumerate, dibutylsuccinate, diethylmalonate, dioctylphthalate, dibutylphthalate, dibutylsebacate, triethyl citrate, tributyl citrate, glyceroltributyrate, polyethylene glycol, propylene glycol and mixtures thereof. The preferred plasticizer is acetyltributyl citrate in an amount ranging from about 1 to about 15 percent based on the total weight of the final coating or 0.1–3% w/w of the total dosage form.

The coating further preferably includes a lubricant such as, but not limited to, those selected from the group consisting of glyceryl monostearate; Myvaplex 600P, calcium stearate or stearic acid. The preferred lubricant is glyceryl monostearate in an amount ranging from about 1 to about 15 percent, and most preferably 1–2.5% based on the total weight of the coating.

A preferred enteric coating for use in the present invention therefore comprises the following ingredients:

| INGREDIENT | PREFERRED | MOST PREFERRED |
|---|---|---|
| HPMCP | 2–10% | 3–5% |
| Acetyltributyl citrate | 0.1–3% | 0.5–1% |
| Glyceryl monostearate | 1–3% | 1–2.5% |

Additional active drug pellets for forming the second coated component of the present invention, preferably from about 90 to about 10 weight percent of the total pellets, more preferably from about 70 to about 30 weight percent, and most preferably from about 67 to about 40 weight percent, are coated with a coating that comprises a polymer such as a methacrylic copolymer, water insoluble polymer, a plasticizer and an anti-sticking agent.

The methacrylic acid copolymer is selected from the known group of methacrylic acid copolymers, preferably Eudragit® S (methacrylic acid copolymer Type B), and most preferably Eudragit® S100. The preferred concentration is 1–15% of the total weight of the dosage form, preferably 4–7%.

The water insoluble polymer in the preferred embodiments of the present invention is formed from a cellulose ester, or a cellulose ester-ether. Representative materials include a member selected from the group consisting of ethyl cellulose, cellulose acylate, cellulose diacylate, cellulose triacylate, cellulose acetate, cellulose diacetate, cellulose triacetate, cellulose acetate butyrate, mono-, di- and tri-cellulose arylates, and the like. Preferred is ethyl cellulose in a concentration ranging from about 1 to about 20%, preferably from about 2 to about 13%.

The preferred plasticizer additive for the second coating may be selected from any of those mentioned above. Acetyltributyl citrate is preferred.

The anti-sticking agents can be chosen from any of the known agents, such as, but not limited to, those selected from the group consisting of an alkaline earth metal stearate, such as magnesium stearate or calcium stearate, or talc. The anti-sticking agents can be used alone or in combination in effective amounts. The preferred anti-sticking agent is talc.

The coating for the active pellet for this (second coated) component of the present invention is applied to the active pellets by forming a solution of the respective coating components in a solvent or a mixture of solvents, such as, but not limited to, acetone and isopropyl alcohol, and employing any of the application techniques known to those skilled in the art, such as fluidized bed coating, rotor granulation or pan coating.

The components, either the two coated or the two coated and the immediate release, of the present invention are blended together in the desired ratio and placed in gelatin capsule to obtain a finished product. By varying the ratio of the three components, including used of the immediate release at 0%, novel dissolution profiles and plasma profiles may be obtained in accordance with the present invention. Alternatively, the dosage formulation may be made into tablets by first adding from 25 to 40 weight percent of a solid pharmaceutically acceptable tablet excipient that will form a compressible mixture without crushing the pellets, and then tabletting the mixture in a suitable tablet press.

The following examples are intended to illustrate the present invention but are not intended to limit the scope of the appended claims.

EXAMPLE 1

A batch of controlled release bupropion was manufacture using all materials that comply with the current USP/NF compendia specifications.

A controlled release 150 mg oral bupropion dosage form is prepared by forming active core pellets having the following composition:

| I. ACTIVE CORE PELLETS | |
|---|---|
| Bupropion HCl | 70.0% |
| Sugar sphere 30/35 | 26.5% |
| Methocel E5 | 3.5% |

Active pellets of bupropion are formed by dissolving 2.8 kg of bupropion HCl and 0.40 kg of hydroxypropyl methylcellulose (Methocel® E5) in a mixture of water and isopropyl alcohol. The active drug solution is then sprayed onto 1.06 kg of sugar spheres 30/35 in a fluidized bed processor with a Wurster insert. The active core pellets are then dried in a fluidized bed processor until the loss on drying is below 1%. The bupropion pellets are then passed through a 16 mesh screen and a 30 mesh screen and pellets are collected that are smaller than 16 mesh and larger than 30 mesh.

| II. ENTERIC COATED PELLETS | |
|---|---|
| Bupropion active pellets | 75.0% |
| HPMCP 50 | 16.9% |
| Acetyltributyl citrate | 2.5% |
| Myvaplex 600P | 5.6% |

For a group of about one-third of the pellets, 0.270 kg of hydroxypropyl methylcellulose phthalate and 0.040 kg of acetyltributyl citrate are dissolved in a mixture of purified water and isopropyl alcohol, USP. Then 0.090 kg of glyceryl monostearate (Myvaplex 600P) is dissolved into the solution above. The solution is then sprayed onto 1.2 kg of the bupropion core pellets in a fluidized bed processor with a Wurster insert. The pellets are then dried until the loss on drying (LOD) is less than 1%. The pellets are then mixed with 2% (w/w) talk for 10 minutes in a V-blender. The pellets are then passed through a 14 mesh screen and a 24 mesh screen and pellets that are smaller than 14 mesh and larger than 24 mesh are collected.

| III. SUSTAINED RELEASE (SR) COATED ACTIVE PELLETS | |
|---|---|
| Bupropion active pellets | 80.0% |
| Eudragit ® S100 | 12.6% |
| Ethocel ® 10 cps | 1.4% |
| Acetyltributyl citrate | 2.0% |
| Talc | 4.0% |

For another group of about two-thirds of the pellets, a coating is prepared where the ratio of the methacrylic acid copolymer to ethylcellulose is about 9:1. The coating is made as follows: 0.378 kg of methacrylic acid copolymer (Eudragit® S 100), 0.42 kg of ethylcellulose (Ethocel® 10 cps), and 0.060 kg of acetyltributyl citrate are dissolved in a mixture of 0.690 kg acetone and 6.210 kg isopropyl alcohol. 0.120 kg of talc is then dispersed into the solution above. The suspension is then sprayed onto 2.40 kg of the active bupropion core pellets in a fluidized bed processor with a Wuster insert. The bupropion pellets are dried in a fluidized bed processor until the LOD is less than 1%. The pellets are mixed with 2% (w/w) talc for 10 minutes in a V-blender and passed through a 14 mesh screen and 24 mesh screen. Pellets smaller than 14 mesh and larger than 24 mesh are collected.

These pellets have the following coating composition:

| INGREDIENT | MG/CAPSULE | % TOTAL WEIGHT |
|---|---|---|
| Eudragit ® S100 | 22.5 | 6.4 |
| Ethocel ® 10 cps | 2.5 | 0.7 |
| Acetyltributyl citrate | 3.6 | 1.0 |
| Talc | 7.1 | 2.0 |

The enteric coated pellets and the SR pellets are mixed after loading each group into dosators. The strength of the final product is 150 mg of bupropion with 50 mg of active drug in the first group of pellets and 100 mg of active in the second group. The pellets are then encapsulated into size "1" light turquoise blue/light turquoise blue capsules. The total weight of the formulation (capsule+pellets) is 350 mg.

The resulting bupropion capsules of Example 1 were then tested according to the USP XXIII dissolution test (type 2, basket) at 50 rpm, at 37° C. in pH 7.5 buffer and found to have the following release profile:

TABLE 1

| Time (hours) | % Released |
|---|---|
| 1 | 25 |
| 2 | 60 |
| 3 | 75 |
| 4 | 80 |
| 6 | 88 |
| 8 | 93 |
| 10 | 93 |
| 12 | 94 |
| 14 | 94 |
| 16 | 94 |

Figure 1:
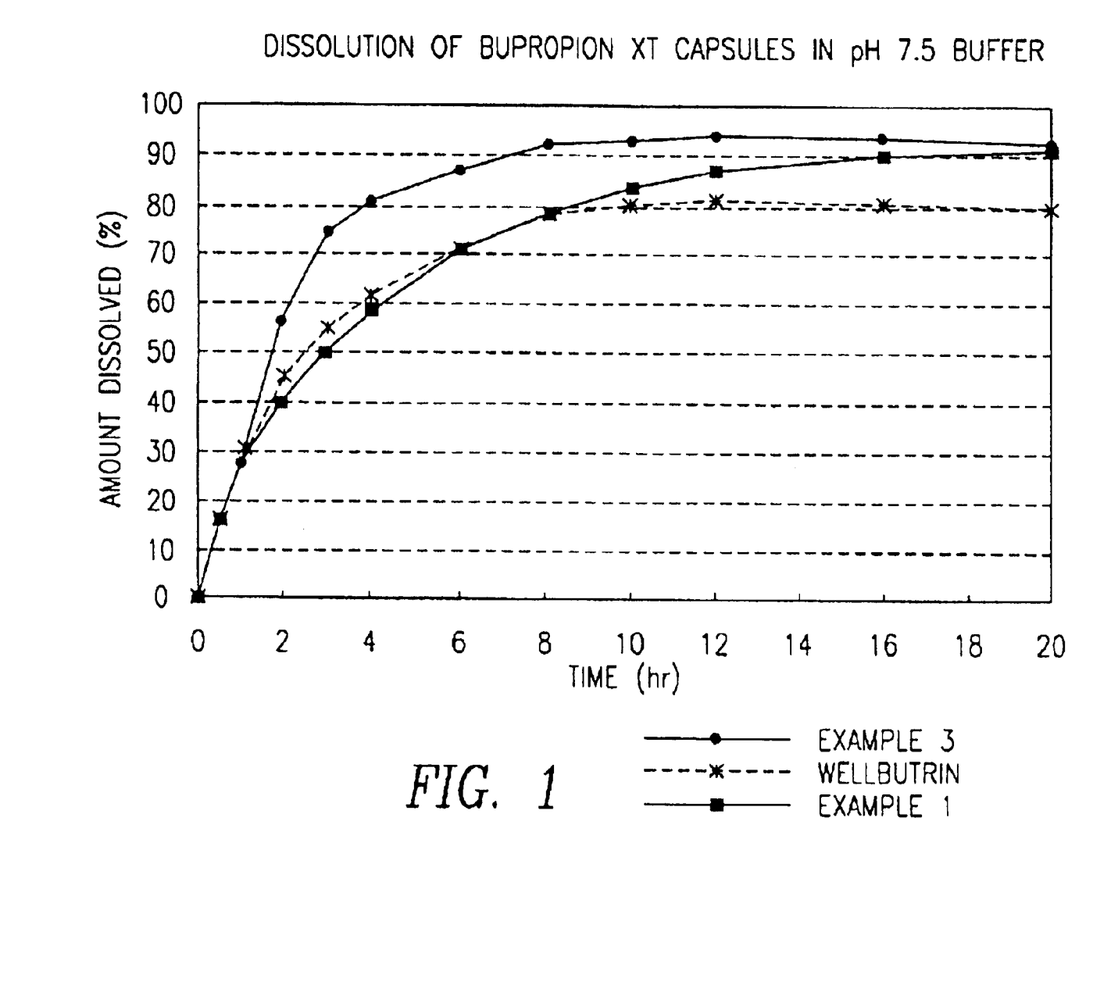
FIG. 1 is a graph depicting the dissolution profile in a pH 7.5 buffer of the formulations as described in Examples 1 and 3 versus the dissolution of the commercially available sustained release form of bupropion (Wellbutrin® SR).

The release profile of the controlled release product shown in this Example is shown in FIG. 1 by the line filled with circles.

The bupropion capsules of Example 1 were then tested according to the USP XXIII dissolution test (type 2, basket), at 50 rpm, at 37° C. in SGF (pH 1.5) to determine the percentage of drug dissolved versus time.

TABLE 2

| Time (hours) | % Released |
|---|---|
| 1 | 0 |
| 2 | 1 |
| 3 | 2 |
| 4 | 3 |
| 6 | 7 |
| 8 | 15 |
| 10 | 30 |
| 12 | 45 |
| 14 | 50 |
| 16 | 56 |
| 20 | 60 |

Figure 2:
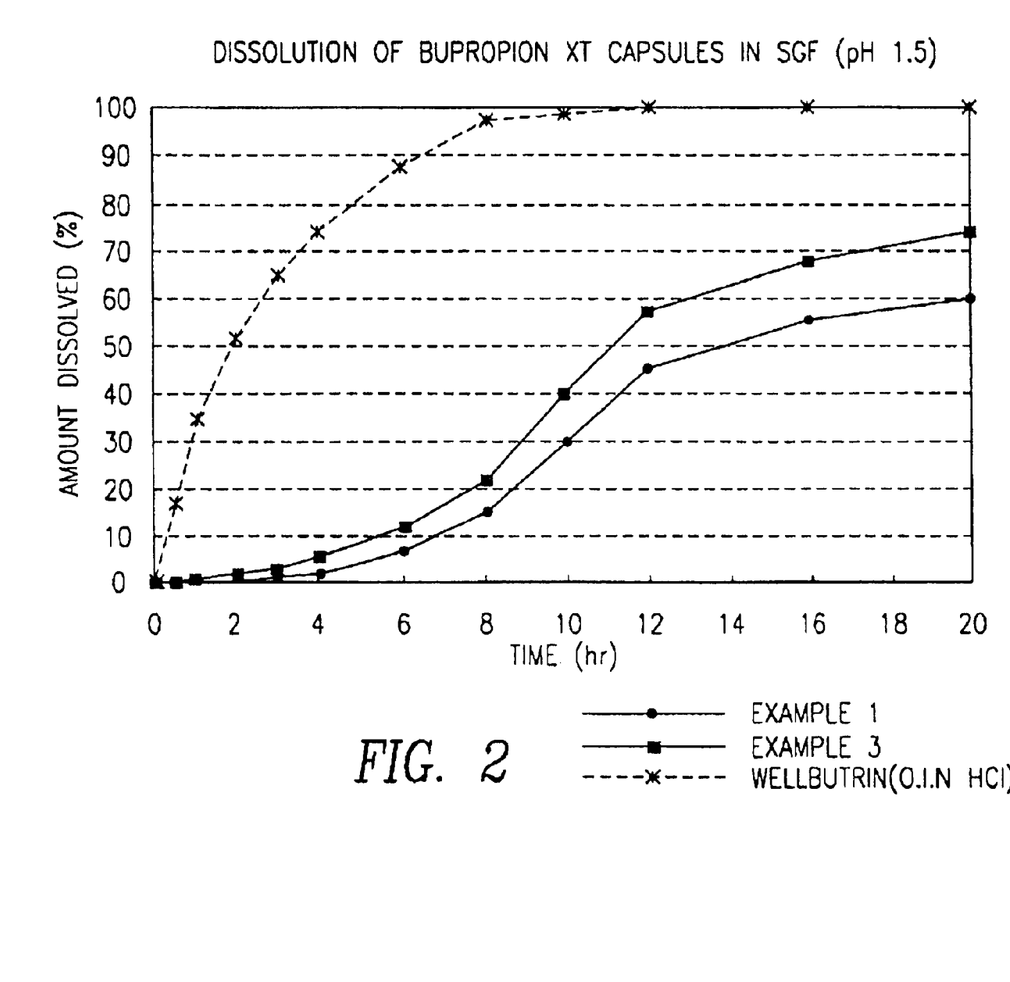
FIG. 2 is a graph depicting the dissolution profile in simulated gastric fluid (pH 1.5) of the formulations as described in Examples 1 and 3 versus the dissolution of the commercially available sustained release form of bupropion (Wellbutrin® SR).

The release profile of the controlled release product shown in this Example 1 is shown in FIG. 2 by the line with the filled circles.

The bupropion capsules of Example 1 were then evaluated in seven patients using standard techniques known in the art. Bupropion was first detected in the plasma at about 2 hours after administration, and showed sustained release over 24 hours.

Two panels of seven patients were randomly assigned to receive either the bupropion formulation described herein or ZYBAN® in an open, randomized single dose study. Blood samples were collected over a 72-hour period and analyzed for bupropion concentrations with a LC/MS/MS method.

Figure 3:
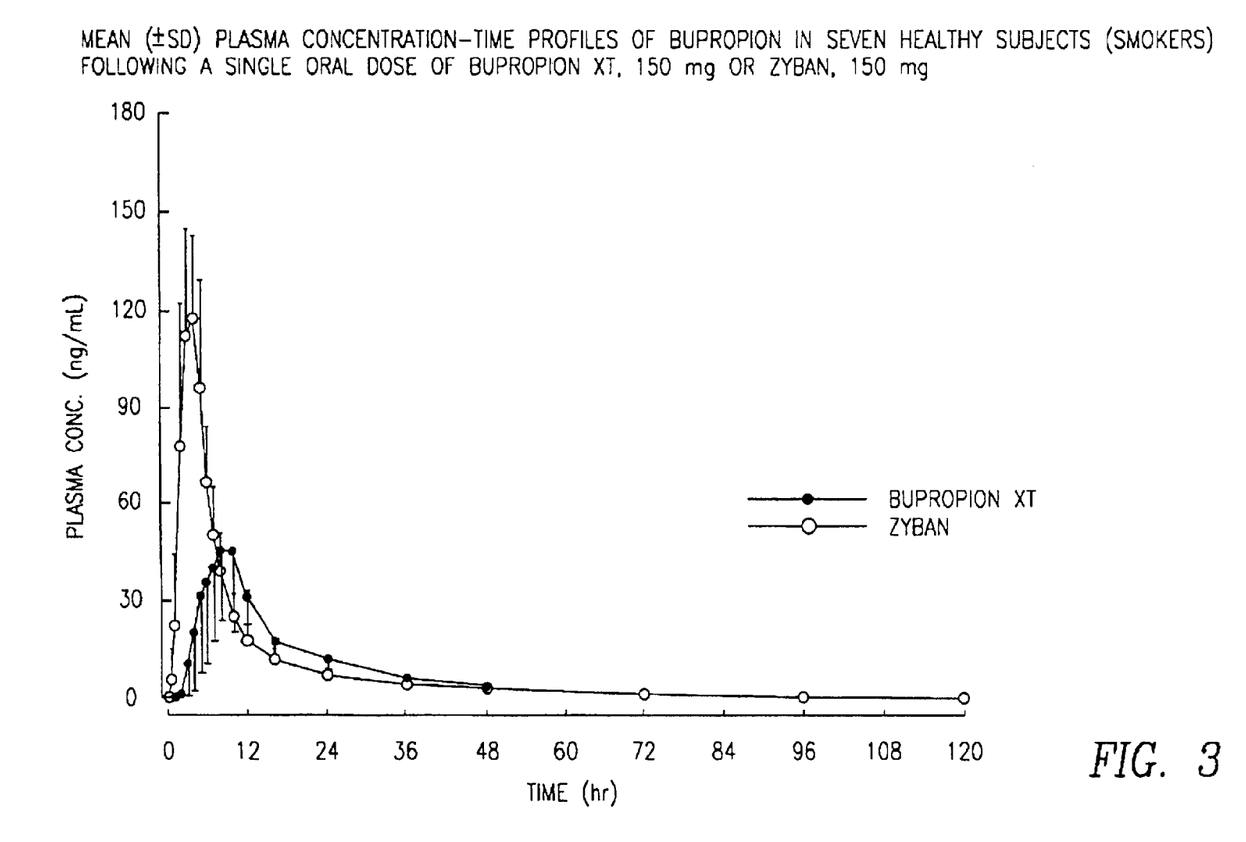
FIG. 3 is a graph depicting the mean plasma concentration-time profiles of bupropion in seven healthy subjects (smokers) following a single oral dose of the formulation in Example 2 versus 150 mg of the commercially available sustained release product (Zyban®).

For the blood levels carried out $C_{max}$ is the maximum blood level concentration, of bupropion, $T_{max}$ is the time at which the maximum blood level concentration occurs, $T_{lag}$ is the sampling point preceding the one at which concentrations first become quantifiable. AUC is the "area under the curve" of time versus blood concentration. The results provided are given in Table 3 and FIG. 3 show that the mean plasma concentration-time profiles of bupropion were different for the Example 1 formulation and Zyban®. Following oral administration, the Example 1 formulation had a delayed absorption with a $T_{lag}$ value of 1.9 hours. The mean $C_{max}$ value of the Example 1 bupropion formulation was about one-half of that for Zyban®. The time to reach ($T_{max}$) maximum plasma concentration occurred about 8 hours after administration of the Example 1 formulation. The relative bioavailability of the Example 1 formulation to Zyban® was 40% in terms of $C_{max}$ and 80% in terms of $AUC_{0-inf}$ ratio.

TABLE 3

| Variable | Example 1 Mean | Zyban Mean | G-Mean Ratio |
|---|---|---|---|
| $C_{max}$ (ng/ml) | 54.2 | 129.0 | 0.40 |
| $AUC_{0-inf}$ (ng · hr/ml) | 832.0 | 998.0 | 0.80 |
| $T_{lag}$ (hr) | 1.9 | 0.1 | |
| $T_{max}$ (hr) | 8.1 | 3.6 | |
| $T_{1/2}$ (hr) | 17.0 | 20.3 | |

Thus, it can be seen from the data above that although the $C_{max}$. Of Example 1 is significantly lower than the $C_{max}$ of the Zyban® formulation, the AUC has only been slightly reduced.

EXAMPLE 2

The pellets from Example 1 are taken as the second and third components. These pellets are loaded into the dosator along with active pellets and are filled into capsules in a ratio of 10:30:60 while maintaining the dosage at 150 mg. The blood profiles from this example will show a $C_{max}$ that is the same as shown in Table 3, but will show a slightly increase AUC, thereby rendering the G-Mean ratio at about 1.00. The amount of active pellets may be adjusted as is known in the art without undue experimentation based on the teachings of the present disclosure in order to substantially provide a G-Mean for AUC of approximately 1.00.

EXAMPLE 3

The procedure of the Example 1 is followed for the first group of pellets. The bupropion cores are prepared by forming a suspension of bupropion and hydroxypropyl methylcellulose in a mixture of water and isopropyl alcohol, which suspension is spray coated onto inert spheres. The HPMCP enteric coating is then applied to about one third of the active drug pellets.

Film Coating for SR Pellets

A second group of about two-thirds of the pellets is coated with a coating prepared where the ratio of methacrylic acid copolymer to ethylcellulose is about 1:1. The pellets have the following composition:

| | |
|---|---|
| Bupropion active pellets | 80.0% |
| Eudragit ® S100 | 7.0% |
| Ethocel ® 10 cps | 7.0% |
| Acetyltributyl citrate | 2.0% |
| Talc | 4.0% |

The coating is made as follows: 0.105 kg of methacrylic acid copolymer (Eudragit® S100), 0.105 kg of ethylcellulose (Ethocel® 10 cps), and 0.030 kg of acetyltributyl citrate are dissolved in a mixture of 0.345 kg acetone and 3.105 kg isopropyl alcohol. 0.060 kg of talc is then dispersed into the solution above. The suspension formed is then sprayed onto 1.20 kg of the active bupropion core pellets in a fluidized bed processor with a Wurster insert. The coated bupropion pellets are then dried in a fluidized bed processor until the LOD is less than 1%. The pellets are mixed with 2% (w/w) talc for 10 minutes in a V-blender and passed through a 14 mesh screen with a 24 mesh screen. Pellets smaller than 14 mesh and larger than 24 mesh are collected.

The pellets have the following coating composition:

| Ingredient | mg/Capsule | % Total Wt. |
|---|---|---|
| Methacrylic acid copolymer | 12.5 | 3.6 |
| Ethocel ® 10 cps | 12.5 | 3.6 |
| Acetyltributyl citrate | 3.6 | 1.0 |
| Talc | 7.1 | 2.0 |

The first group of pellets and the 1:1 above pellets are mixed after loading each group into dosators. The strength of the final product is 150 mg of bupropion with 50 mg of active drug in the first group of pellets and 100 mg of active drug in the second group. The pellets are then encapsulated into size "1" buff opaque/light blue opaque capsules. The total weight of the formulation (capsule+pellets) is 352 mg.

The resulting bupropion capsules were then tested according to the USP XXIII dissolution test (type 2, basket), at 50 rpm, at 37° C., in pH 7.5 buffer and found to have the following release profile:

| Time (hours) | % Released |
|---|---|
| 1 | 28 |
| 2 | 40 |
| 3 | 50 |
| 4 | 58 |
| 6 | 70 |
| 8 | 80 |
| 10 | 83 |
| 12 | 87 |
| 14 | 88 |
| 16 | 90 |
| 18 | 90 |
| 20 | 92 |

The release profile of the controlled release product of Example 3 is shown in FIG. 1 by the line with the filled in squares.

The resulting bupropion capsules were then tested according to USP XXIII dissolution test (type 2, basket), at 50 rpm, at 37° C., in SGF (pH 1.5) and found to have the following release profile:

| Time (hours) | % Released |
|---|---|
| 1 | 0 |
| 2 | 2 |
| 3 | 4 |
| 4 | 6 |
| 6 | 12 |
| 8 | 21 |
| 10 | 40 |
| 12 | 57 |
| 13 | 64 |
| 16 | 68 |
| 17 | 71 |
| 20 | 74 |

The release profile of the controlled release product shown in Example 3 is shown in FIG. 2 by the line with the filled in squares.

The bupropion capsules of Example 3 were then analyzed in a seven patient test using techniques known in the art. Bupropion was first detected in the plasma about 1.4 hours after administration and showed a sustained release over 24 hours.

Figure 4:
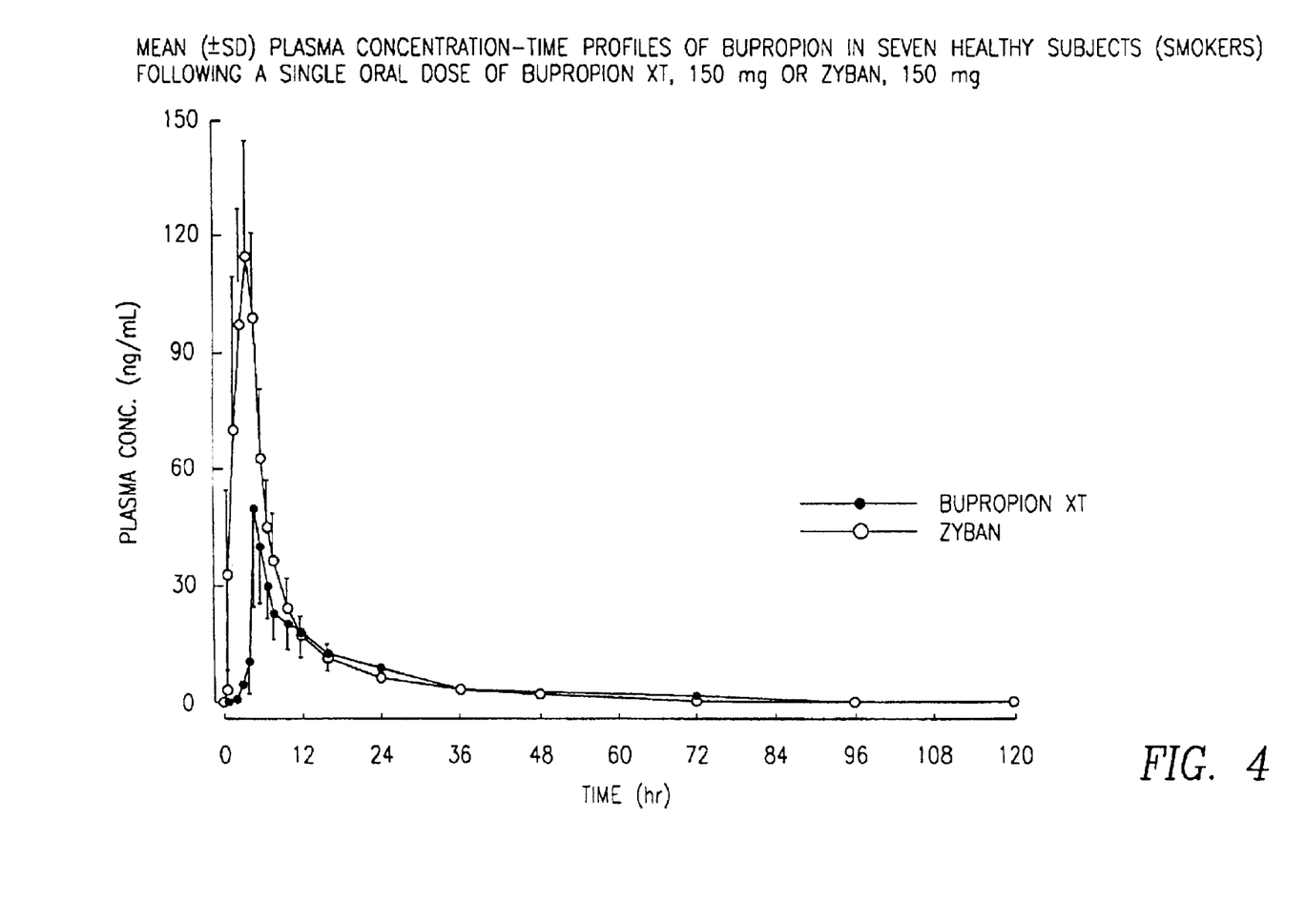
FIG. 4 is a graph depicting the mean plasma concentration-time profiles of bupropion in seven healthy subjects (smokers) following a single oral dose of the formulation in Example 4 versus 150 mg of the commercially available sustained release product (Zyban®).

The testing procedure is as described in Example 1. The results provided are given in Table 4 and FIG. 4 and show that the mean plasma-time profile of the bupropion formulation differs from that of Zyban®. Bupropion had a delayed absorption; the relative bioavailability of bupropion to Zyban® was 48% and 59% in terms of $C_{max}$ and AUC values, respectively. The terminal elimination half-lives were similar.

TABLE 4

| Parameter | Example 3 | Zyban ® | G-Mean Ratio |
|---|---|---|---|
| $C_{max}$ (ng/ml) | 56.9 | 114.8 | 0.48 |
| $AUC_{0-inf}$ (ng · hr/ml) | 531.7 | 889.5 | 0.59 |
| $T_{lag}$ (hr) | 1.4 | 0.1 | |
| $T_{max}$ (hr) | 5.1 | 4.1 | |
| $T_{1/2}$ (hr) | 12.6 | 14.1 | |

Thus, again, the $C_{max}$ of the Example 3 product was reduced significantly more than the AUC compared to the reference product, demonstrating that an effective once-a-day product has been provided.

EXAMPLE 4

The pellets from Example 3 are taken as the second and third components. These pellets are loaded into the dosator along with active pellets and are filled into capsules in a ratio of 10.30:60 while maintaining the dosage at 150 mg bupropion. The blood profiles from this example will show a $C_{max}$ the same as in Table 3, but will show a slightly increased AUC, thereby rendering the G-mean ratio at about 1.00. The amount of active pellets may be adjusted as is known in the art without undue experimentation based on the teachings of the present disclosure in order to substantially provide a G-Mean for AUC of approximately 1.00.

While certain preferred and alternative embodiments of the invention have been set forth for purposes of disclosing the invention, modifications to the disclosed embodiments may occur to those who are skilled in the art. Accordingly, this specification is intended to cover all embodiments of the invention and modifications thereof that do not depart from the spirit and scope of the invention.

All of the above-identified patents are hereby incorporated by reference.

What is claimed is:

1. A once daily dosage form comprising 150 mg of an bupropion or salt of bupropion, said dosage form providing an in vivo plasma profile selected from:

(a) Mean $T_{max}$ of about 5 or more hours
   (b) Mean $C_{max}$ of less than about 90 ng/ml, and
   (c) Mean $AUC_{0-120h}$ of more than about 350 (ng-h)ml.

2. The once daily dosage form of claim 1 wherein said mean $C_{max}$ is less than about 80 ng/ml.

3. The once daily dosage form of claim 1 wherein said mean $C_{max}$ is less than about 70 ng/ml.

4. The once daily dosage form of claim 1 wherein said mean $C_{max}$ is less than about 60 ng/ml.

5. The once daily dosage form of claim 1 wherein said mean $C_{max}$ is less than about 50 ng/ml.

6. The once daily dosage form of claim 1 wherein said mean $C_{max}$ is less than about 40 ng/ml.

* * * * *